United States Patent [19]

Sommerich

[11] Patent Number: 5,782,286
[45] Date of Patent: Jul. 21, 1998

[54] METHOD OF CASTING HOLLOW BONE PROSTHESIS WITH TAILORED FLEXIBILITY

[75] Inventor: Robert E. Sommerich, Norton, Mass.

[73] Assignee: Johnson & Johnson Professional, Inc., Raynham, Mass.

[21] Appl. No.: 764,895

[22] Filed: Dec. 16, 1996

Related U.S. Application Data

[62] Division of Ser. No. 536,816, Sep. 29, 1995, Pat. No. 5,725,586.

[51] Int. Cl.$^6$ .......................... B22D 25/00; B22D 29/00
[52] U.S. Cl. .................................... 164/132; 164/519
[58] Field of Search ........................ 164/132, 47, 516; 623/901

[56] References Cited

U.S. PATENT DOCUMENTS

| | | | |
|---|---|---|---|
| 3,893,196 | 7/1975 | Hochman | 3/1.91 |
| 4,287,617 | 9/1981 | Tornier | 3/1.913 |
| 4,314,381 | 2/1982 | Koeneman | 3/1.912 |
| 4,375,282 | 3/1983 | Herold | 164/369 X |
| 4,595,393 | 6/1986 | Anapliotis et al. | 623/22 |
| 4,718,914 | 1/1988 | Frey et al. | 623/23 |
| 4,756,711 | 7/1988 | Mai et al. | 623/23 |
| 4,808,186 | 2/1989 | Smith | 623/23 |
| 4,832,107 | 5/1989 | Hass et al. | 164/132 X |
| 4,921,501 | 5/1990 | Giacometti | 623/23 |
| 4,944,759 | 7/1990 | Mallory et al. | 623/22 |
| 4,944,761 | 7/1990 | Stuhmer et al. | 623/23 |
| 5,015,817 | 5/1991 | Kranz | 219/121.14 |
| 5,019,106 | 5/1991 | Willert | 623/22 |
| 5,021,063 | 6/1991 | Täger | 623/23 |
| 5,047,060 | 9/1991 | Henssge et al. | 623/23 |
| 5,092,899 | 3/1992 | Forte | 623/23 |
| 5,178,201 | 1/1993 | Ahlers | 164/34 |
| 5,330,536 | 7/1994 | Täger et al. | 623/23 |
| 5,535,810 | 7/1996 | Compton et al. | 164/45 X |

FOREIGN PATENT DOCUMENTS

| | | | |
|---|---|---|---|
| 0390768 | 10/1990 | European Pat. Off. | 623/23 |
| 3844157 | 6/1990 | Germany | 623/23 |

OTHER PUBLICATIONS

Uziel, Y., "Art to part in 10 days", Machine Design, (1995), pp. 56–58, 60.

Primary Examiner—J. Reed Batten, Jr.
Attorney, Agent, or Firm—Nutter, McClennen & Fish, LLP

[57] ABSTRACT

The stem is cast about an irregular plug body, which is then removed, leaving a wall thickness that satisfies the opposing constraints of high strength and relatively low stiffness. The plug narrows the prosthesis wall thickness in upper regions thereof and strengthens the wall about regions of recessed or discontinuous features, or high load coupling, to assure that the stem has adequate strength in regions of high strain, while effectively coupling strain to surrounding bone. The prosthesis is produced in a range of sizes, and plugs or entire molds for casting the hollow body are readily made and modified by a three-dimensional printing mold fabrication technique.

5 Claims, 8 Drawing Sheets

METHOD OF CASTING HOLLOW BONE PROSTHESIS WITH TAILORED FLEXIBILITY

This application is a division of application Ser. No. 08/536,816, filed Sep. 29, 1995, and now U.S. Pat. No. 5,725,586.

BACKGROUND

The present invention relates to bone prostheses and specifically to implants of the type having a long body which is fitted into or against a natural bone to repair or replace all or part of a bone or joint, and which is coupled to the bone to transfer its load therealong. By way of example, this may be an intramolecular stem, such as is commonly used to provide the femoral ending component of a hip joint. Such a prosthesis has a long tapered body which fits into a bore of corresponding size that has been drilled and broached in the femur, and the prosthesis is secured in place by one or more of frictional engagement, cement, and ultimately, new bone growth.

It has long been realized that when a prosthesis of this type is too stiff, as generally occurs in the upper region, it is unable to transfer any stress to surrounding bone, with the result that the bone in that region suffers "stress shielding" and is gradually resorbed. This effect is local; near the distal end where the prosthesis is thinner and more flexible, this bone loss from stress shielding generally does not occur. At the thicker top portion of the stem, the stem itself bears all the load, and since it is so strong as to have virtually no bending deflection, little strain is transferred to surrounding bone and bone in that region is very prone to resorption and loss of mass. While this problem has been recognized for quite some time, there is an inherent tradeoff between, on one hand, the desirable traits of strength, freedom from defects and longevity of a bone implant, and, on the other, the requirement that the prosthesis be shaped such that it not take over bone function so completely as to cause withering of the natural bone. A number of approaches have been suggested to alleviate stress shielding, including the provision of a stem body with a layer of elastomeric material disposed between and attaching to at least two sections of rigid material, or one having rings of elastic material disposed around the stem, as shown in U.S. Pat. No. 4,314,381.

Others have suggested forming a prosthesis with weakened portions to adapt its longitudinal rigidity or bending resistance to that of the surrounding bone (U.S. Pat. No. 4,595,393), or forming a stem with a channel that varies the wall thickness along the length to achieve flexibility (U.S. Pat. No. 4,808,186). A number of other patents show hip prostheses in which a hollow stem is formed of two mating half members; show a perforated tube-like body; or show another construction in which the body is generally hollowed or thinned. In particular, U.S. Pat. No. 5,092,899 shows a prosthesis with a flexible intramedullary stem made by forming a tapered bore centrally in an otherwise conventionally shaped solid stem. The taper is aligned such that one wall is of substantially uniform thickness for the full height of the stem, while the other wall directly below the ball tapers from a relatively thick body at its top end to a relatively thin wall at the distal end.

These developments represent a dramatic change from the early manufacture of bone prostheses in that rather than being designed with maximal strength to assure it is sufficiently strong and rigid to entirely replace bone and bear the full loading and impact of use for a number of years, the prosthesis is now expected to have such strength and longevity, but also to have bending and strain transfer characteristics such that the supporting bone is stimulated and grows strong. In practice, constructions proposed for enhancing strain transfer may adversely affect strength or longevity; for example, a two-piece construction may be weaker along the junction of the pieces.

Furthermore, in many existing solid prosthesis constructions, the distal tip has been found to transmit adequate strain to surrounding bone to stimulate normal bone growth. Thus, as a practical matter, the above insights may involve simply modifying the upper, i.e., proximal, portion of the stem to achieve a somewhat more extended distribution of proper strain coupling. However, since the proximal end of the stem must have great strength to couple to a load-bearing joint, and since any assumption of the bone loading by the prosthesis results in diminished bone growth, the design of a prosthesis that adequately carries the weight and yet maintains an effective level of loading on the surrounding bone remains problematic. This is especially true since the proximal end of the stem must be of relatively large diameter to fit the intramedullary space. In general, it may be said that distribution of the load transferred from the acetabulum to the stem is difficult to model, and the mechanics of the stem when inserted in the femur may vary depending upon size of the stem and the nature and closeness of the fit to surrounding bone. Furthermore, when the prosthesis has variations in outer surface contour or texture its mechanical properties become difficult to model and a greater margin of safety must be provided to assure freedom from geometry- or impact-induced failure. For these reasons, the desired goal of inducing strain in the surrounding bone does not, of itself, suggest any particular construction. Accordingly, there remains a need for a bone prosthesis having a longitudinal body which has a structural strength for dependably bearing the load from a bone or a joint, yet has a bending compliance which effectively transfers strain to surrounding bone and prevents stress shielding along its length.

SUMMARY OF THE INVENTION

These and other desirable features are obtained in a prosthesis of the present invention by providing a stem body in the form of a generally elongated spike which fits within a bone and bears against the inner surface thereof to firmly anchor the spike therein. The prosthesis includes an element, such as a ball or platform of an articulation at its proximal end, which couples to or receives a load, and it extends to a distal end such that the end generally aligns and secures the prosthesis within surrounding bone. The outer surface of the stem may have textured regions of known type for promoting bone growth and engagement with the bone, and may have surfaces wedging against surrounding bone or strongly engaging a cement for fixation thereto. However, the stem also has an inner surface, which varies irregularly forming at least in part, a hollow and generally cylindrical but irregular member.

The outer surface may have a machine-like symmetry, e.g., may be approximately a rounded-edge rectangular or trapezoidal spike of small taper, which is installed in a corresponding recess formed in the bone by a tapered broach or other mechanical cutting implement for forming a precise fit thereto. The contour of the inner surface of the metal prosthesis on the other hand is characterized by a lack of machine symmetry and forms in cross-section a contour which is neither geometric, nor in general even parallel to the outer contour. In general, as discussed further below, the inner contour optimizes flexural compliance by varying wall thickness globally and locally to simultaneously accommodate regions of high load or bending stress while allowing the prosthesis as a whole to effectively match its load to surrounding bone.

In a preferred embodiment, the prosthesis is an intramedullary stem, and is characterized by an elongated body having a head portion, a transition portion and stem end portion. The stem end portion is roughly symmetric and tapered, while the head and transition portions are highly irregular in shape, of greater diameter, and hollow. The prosthesis is a metal object cast in a mold, with the outer surface defined by the contour of a mold cavity while the inner surface is defined simultaneously during the casting step by a plug insert set in the mold. Alternatively, it may be cast with an oversize outer contour, with subsequent machining and polishing of the exterior to a final size and finish. In each case, at each distance along the prosthesis, the stem has a wall thickness determined by the difference between the outer contour and the diameter of the mold plug insert at that distance, and thus forms a shell of irregular inner contour. The wall thickness thus defined is variable, both along the height and circumferentially of the prosthesis.

By comparison to a conventional solid or counter-bored stems, in general the variation achieved in the present invention reduces the wall thickness particularly at the top, and may either reinforce or reduce wall thickness at one or more mid positions of the prosthesis, as discussed below. This results in a bending stiffness along the length of the prosthesis which is substantially uniform over a major portion of its length and rises slowly approaching the collar at the proximal end. Furthermore, the axial stiffness is substantially uniform and approximates a linear function with low slope. For example, for a twelve millimeter stem of the present invention, the axial stiffness lies between two and four $e^8 mm^4 \times N/mm^4$, and the bending stiffness between about onehalf and eight $e^9 mm^4 \times N/mm^2$. For larger diameter tapered stems, the corresponding stiffnesses are slightly larger, but again substantially uniform or of the same order as the corresponding stiffnesses of native femoral bone.

As noted above, the inner contour of the prosthesis follows an irregular surface contour, and this may be one in which front to back and side to side profiles differ. Reference is made to the paper of A. R. Dujovne, et al. *Mechanical Compatibility of Noncemented Hip Prosthesis with the Human Femur* (1993) for a general description of the measured stiffnesses and mechanical properties of human femoral bones; that paper also has identification of typical mechanical engineering equations useful for calculation of the stiffness of irregular beam shapes which may be used for modeling these prostheses. The prosthesis of the present invention has a stiffness generally somewhat higher than that reported in that paper for the human femur. However, the walls of the prosthesis are thinned, especially in the upper region, to result in a stiffness significantly lower than those reported in that article. Furthermore, the walls are selectively thickened at reinforcement regions to prevent stress cracking without significantly increasing overall stiffness of the prosthesis. These properties are attained without altering the external contour.

This is achieved in a preferred method of manufacture in accordance with the present invention by providing an external mold cavity having an inner bounding wall substantially identical to the outside of the desired prosthesis, and providing an inner mold insert in the cavity shaped like a plug having an irregular contour and specific dimensions such that its outer wall defines the inside of the prosthesis.

The prosthesis is cast in the remaining unoccupied space of the mold cavity around the plug insert. The plug insert is preferably formed by a process of three-dimensional printing, as described, for example, in U.S. Pat. No. 5,204,055 of Sachs et al. and in commonly-owned U.S. patent application Ser. No. 08/198,874 filed Feb. 18, 1994, and now abandoned. The plug has its outer contour configured, in relation to the contour of the outer mold, so that it defines a wall thickness that reinforces indented or highly stressed areas, and generally defines a prosthesis body with walls or cylindrical "plates" that maintain an overall axial or bending stiffness that is low and substantially uniform. In particular, wall thickness decreases with increasing radius of the prosthesis, to as little as two or three millimeters, while it increases behind surface recesses or abrupt edges of the outer surface to provide a generally smooth thickening reinforcement at the inner surface; wall thickness generally also increases in regions of smaller diameter. In a related method of manufacture, the hollow prosthesis may be cast with a rough and oversized outer surface; that surface is then shaped by machining operations to provide a desired tapered external profile with the casting process providing only the irregular inner wall contour.

BRIEF DESCRIPTION OF DRAWINGS

The invention will be understood from the discussion below taken together with illustrative drawings, wherein.

DETAILED DESCRIPTION

Figure 1:
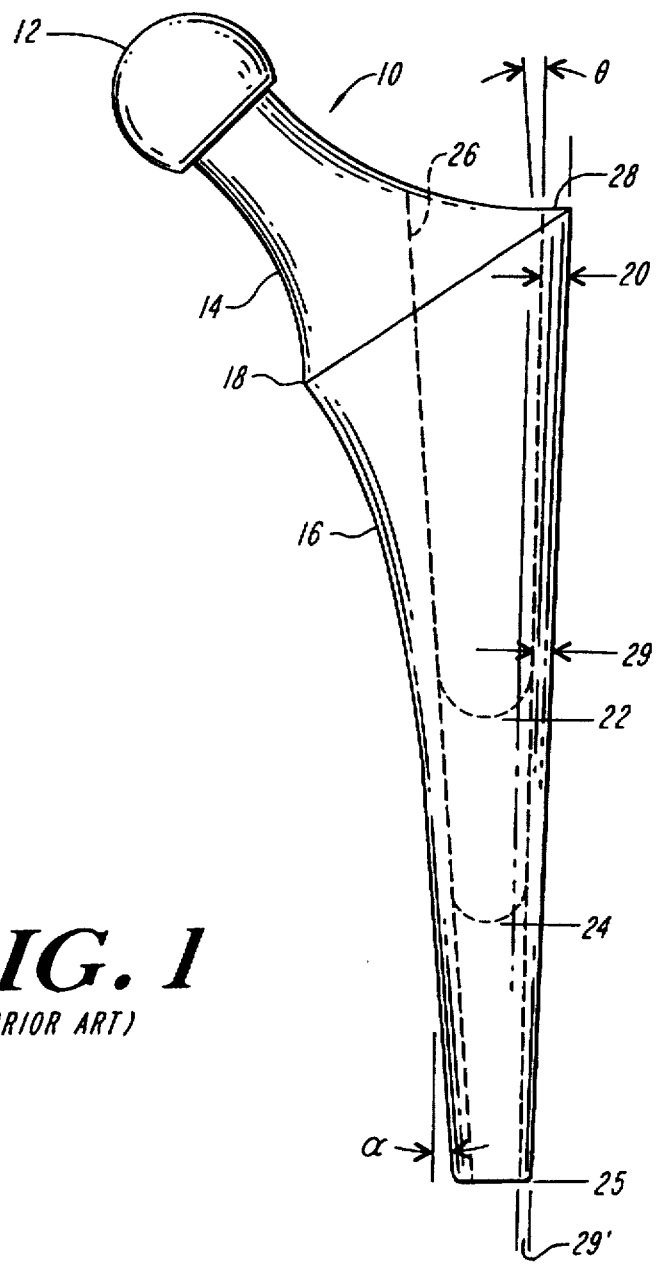
FIG. 1 shows one conventional hip prosthesis.

FIG. 1 shows a prior art intramedullary stem hip prosthesis such as has been proposed in U.S. Pat. No. 5,092,899. The prosthesis has a femoral head 12 attached at a neck portion 14 to a stem 10, via a generally large and contoured transition joint 18 and shoulder 16. The stem 10 has a generally tapered and elongated body with at least a lower portion tapered at a small but fairly regular angle which is specified in that patent to be under approximately five degrees and adapted to fit securely within a suitably prepared central bore in the femur of a patient. A comparably tapered internal bore 26 extends axially through the center of the stem, either partially along the length to an intermediate depth 22 or 24, or fully through the end 25. The difference between the outer contour and the inner bore defines a wall thickness 20, 29, or 29', which may be either uniform, as shown on the lateral side or different at different places along the length, as appears in the medial side. The device of FIG. 1 may be contrasted with, for example, a conventional solid prosthesis, having a somewhat similar outer contour but no interior hollow, and which therefore is more rigid. As shown, the position of the bore in the device of FIG. 1 is utilized to thin out the walls in an upper region or even along the entire length of the device and make it more flexible. However, the use of a uniformly tapered bore within an irregular and partly geometric outer taper contour provides a constraint on the degree of flexibility that can be attained at different points along the length while maintaining a given degree of structural strength. Furthermore, such prostheses are normally provided in a range of sizes to fit, for example, within a 12 mm, 13 mm, or even a 15 or 16 mm hollow in the femur. The actual stiffness of each of the prior art solid prosthesis differs, and it is not clear whether any value is gained by thinning the upper portion of a prosthesis in a manner proportionate or linearly related to the thinning occurring in a lower portion. Indeed, while the construction of FIG. 1 definitely provides a reduced wall thickness over the prior art, it is not clear whether such a tapered reduction is either effective to stimulate bone in the upper region, or helpful in any way in the lower region, for a given size of prosthesis.

Figure 1A:
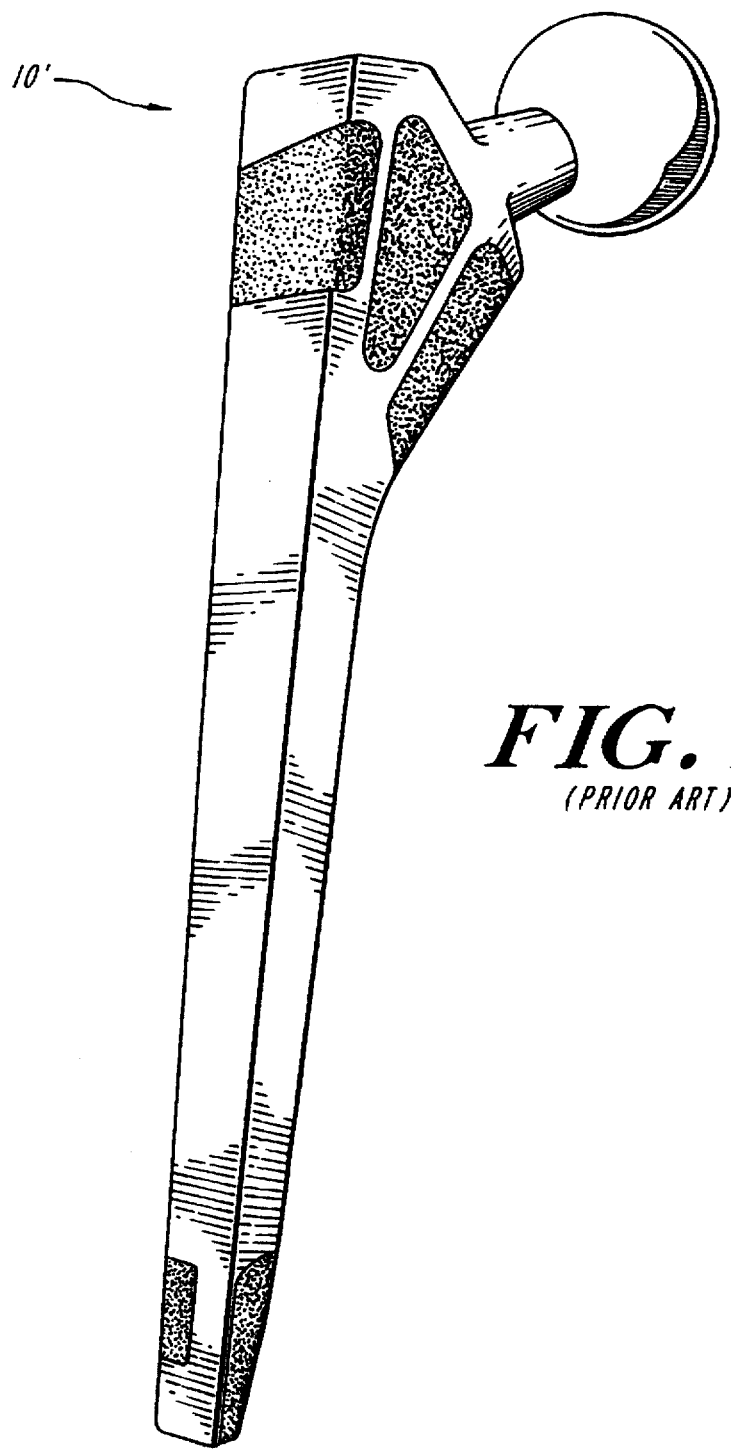
FIG. 1A shows another conventional hip prosthesis.

FIG. 1A shows, by way of further background a conventional prosthesis 10' of solid construction. This prosthesis has been widely marketed by Johnson & Johnson, and includes regions of surface texture 30, near the ends for enhanced bone coupling, as discussed further below. Its outer contour is somewhat similar to that of the device of FIG. 1, and includes an elongated portion configured to fit closely within a prepared medullary opening.

Figure 2:
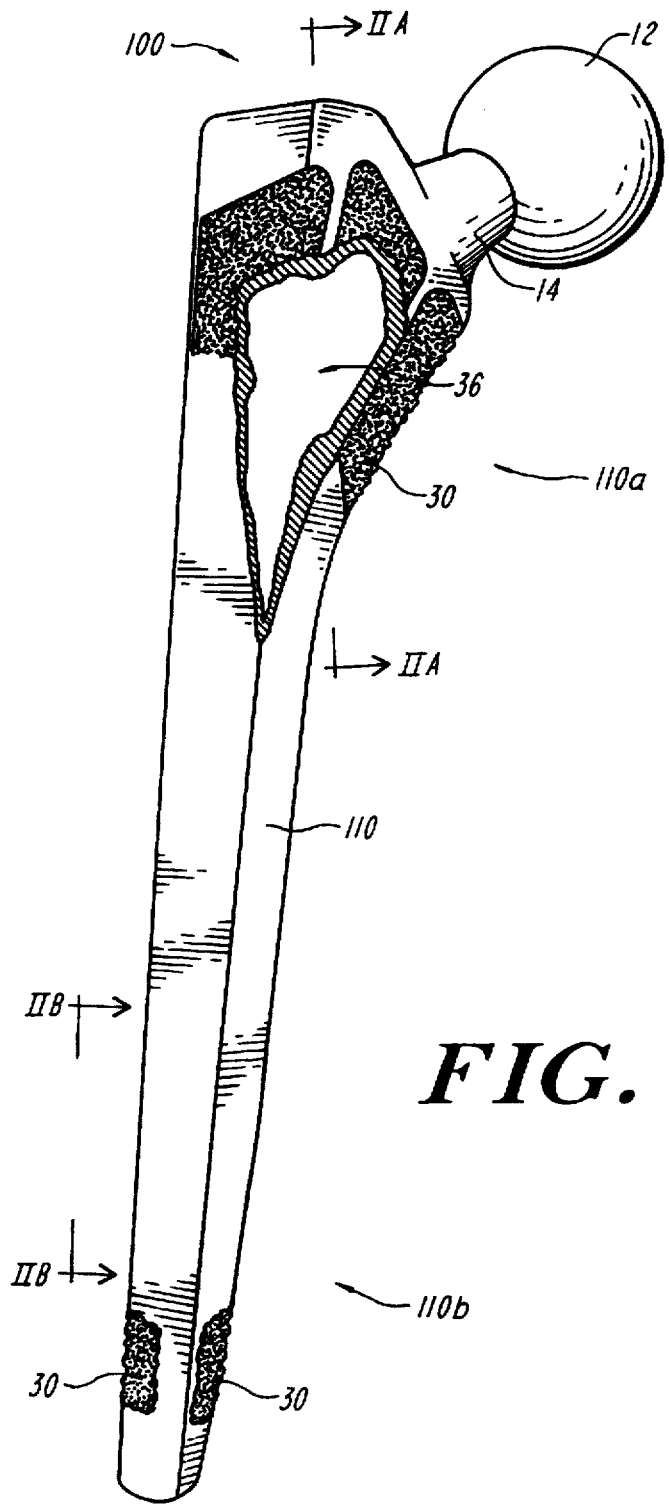
FIG. 2 shows a prosthesis in accordance with the present invention.

FIG. 2 shows a prosthesis 100 in accordance with the present invention applied to the prosthesis of FIG. 1A. In this embodiment, a stem 110 is substantially identical, for example, in its outer contour to that of the body 10' of the prosthesis FIG. 1A, but is modified by having an irregular hollow 36 extending centrally at least partially therethrough. Unlike bore 26 of the prior art article of FIG. 1, the hollow 36 is not a machined boring, but rather is an irregularly-shaped void that provides a non-linear hollowing of the interior of the prosthesis 100 with a thin-walled proximal end, and preferential thickening of the prosthesis wall at one or more positions along its length. Furthermore, the hollowing provides a net wall thickness in the range of about two to seven millimeters, such that substantially the entire prosthesis below the joint mounting, i.e., below femoral head 12 and neck or post 14, is a thinned-shell or somewhat bendable shaft. With this construction, forces exerted at or through the articulation hip ball or ball mounting post, cause a distributed strain field throughout the surface regions of the prosthesis which are to contact surrounding bone. In particular, the shell has a thickness such that axial and bending stiffness of the prostheses are of the same order of magnitude, even in the collar and shoulder regions of the prosthesis, as the natural axial and bending stiffness of the femur in which the prosthesis is to be inserted or embedded. Furthermore, this is achieved without excessively diminishing the strength of the prosthesis in the upper area, without altering the outer surface, and preferably with selective thickening in localized areas of high strain.

The embodiment shown in FIG. 2 is a metal prosthesis having a number of rough or textured surface patches 30 disposed at the distal end and the proximal shoulder regions, and optionally in other intermediate positions (not shown) along the stem 110. These textured outer surface regions may be of known type, and basically provide regions of porous surface relief which couple with very high shear strength attachment to newly-growing bone. These textured regions may be formed in a number of ways, such as by directly casting the prosthesis in a textured mold, separately machining a texture onto the surface of an already-cast prosthesis, or brazing or welding-on separate beads or wires of material; such texturing constructions do not require detailed description. However, as pertinent to the present invention, one specific construction will be described in which the textured patches 30 are formed by originally forming the prosthesis with pockets or recesses corresponding to the region of each patch 30, wherein the surface is recessed approximately one millimeter to form a shallow pool or tray. Texture is then created in the tray by placing metal beads or grains in the tray and heating the assembly to weld or melt the beads or grains onto its recessed surface.

Figure 2A:
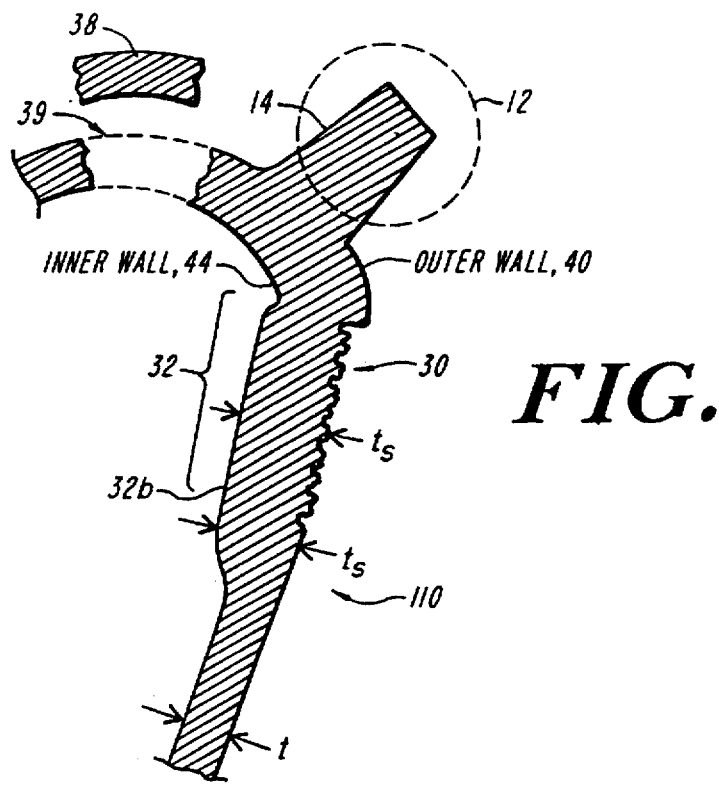
FIGS. 2A and 2B are sections taken along the longitudinal axis of the prosthesis of FIG. 2 at end portions thereof.

FIG. 2A shows the prosthesis 100 in a section through such a textured patch 30, illustrating representative contours of the inner wall 44 of the hollow interior in accordance with a preferred embodiment of the present invention, and showing the exterior wall 40 of the prosthesis. Walls 44 and 40 together define the wall thickness t at each point. As shown, behind the outer recess or bead pocket defining the textured patch 30, a support portion 32 of the wall extends with increased thickness $t_s$ to accommodate the high stresses which will be transmitted to bone in this area, while the thickness $t_r$ may be as great or greater at and beyond the distal portion of the outer pocket to define a thickened band 32b in that more highly strained, load-bearing region. As shown, this portion extends beyond the abrupt indentation forming the pocket edge, allowing the prosthesis wall to maintain uniformly high strength, while nonetheless distributing the load to thinner walls surrounding the pocket and providing a relatively low level of bending stiffness throughout.

Thus, rather than providing a regular hollow interior contour that is set below the maximal indentation, in general, the inner wall 44 follows a contour below the outer surface of the neck to assure a relatively thick collar, providing a strong, well-supported transfer of the load into the hollow stem, while thinning out to distribute strain in a hollow shell of reduced thickness in the regions below the shoulder extending into the femur. The thickness of this shell varies, being in general thinner where the stem is of larger diameter, and as noted above, selectively thicker in regions of high stress or where load transfer to surrounding bone is to be preferentially reduced. The wall may also be thickened in regions where bending deflection is highest, e.g., toward the midpoint of the stem.

Figure 2B:
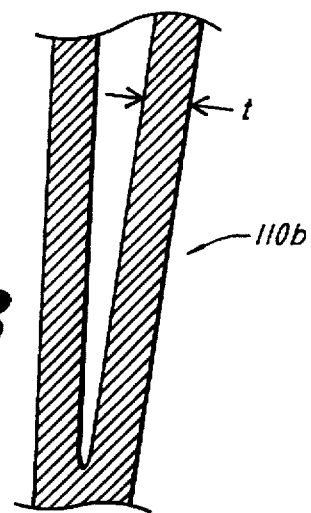

FIG. 2B shows a corresponding section in the lower, or distal, region 110b of the stem 110. In that region the overall stem diameter is much less than that of the proximal end, e.g., under half as great, and the inner wall 44 defines a much thicker prosthesis wall thickness t. This thickness may be, for example, three to six millimeters, whereas the thickness just below the reinforcement 32b in the proximal region may be from about two to four millimeters. Indeed, the hollow 36 may entirely terminate above region 110b, so that the distal end is entirely solid, at least for the smaller gauge stem sizes on the order of twelve millimeters. The precise inner diameter for each stem size may be selected by employing beam modeling to achieve the stiffness illustrated in FIGS. 6 and 6A.

Also shown in FIG. 2A is a cap piece 38 which closes the hollow prosthesis. Cap 38 may also include a striker surface, that is struck to tap the stem into position when installing it in the femur. The wall thickness around the cap 38 is also substantial to assure that no cracks or deformations occur in the casting or cap during assembly or implantation.

Figure 3:
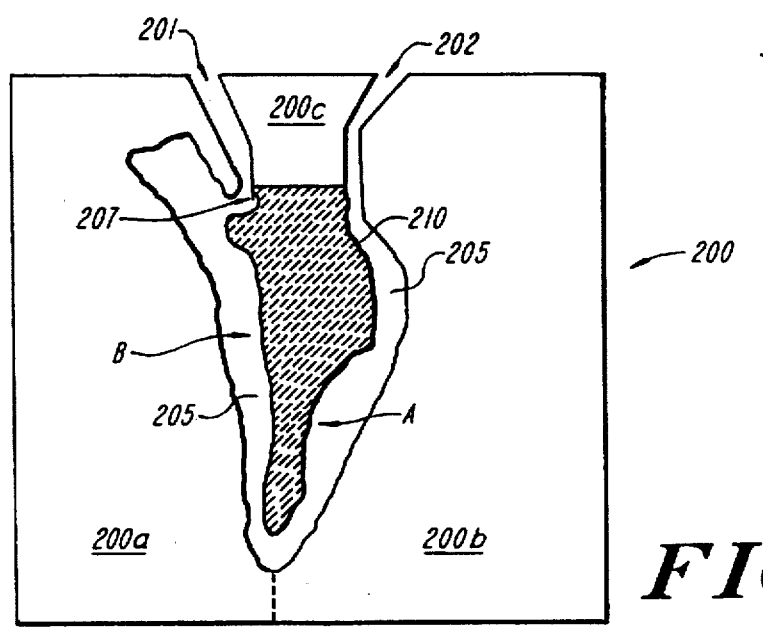
FIG. 3 illustrates a mold for the production of the prosthesis of FIG. 2.

FIG. 3 schematically shows a casting mold 200 used for forming the prosthesis 100. As shown, the mold 200 comprises mold block including separable halves 200a, 200b and an inlet-defining portion 200c which together form a closed cavity in which the prosthesis is cast via inlets 201, 202 as well as breather passages or sprues (not shown) of conventional type, which together allow the cavity 205 to entirely fill with molten metal. Within the cavity 205, a filler body or plug insert 210 formed of refractory material defines a central region which does not fill with metal, and which corresponds in size and shape, after accounting for thermal expansion, to the hollow interior of the finished prosthesis shown in FIG. 2. As shown, the filler body 210 is highly irregular, bulging out below the neck 207 of the casting mold cavity to generally follow the outer contour, but also defining a thickened support wall in the region corresponding to the post on which the hip ball mounts in the finished prosthesis. This provides a hollowing out of the prosthesis in a manner to generally leave a web or sheet of casting material structurally supporting the protruding post (14, FIG. 2) and dimensioned to receive the load distributed thereto. Furthermore, the filler body 210 narrows appreciably at an intermediate position A along its length which corresponds roughly to a region of increased strength having both reduced flexibility and reduced strain in the elongated thinner portion of the finished prosthesis. The narrowing at region A of the filler body produces a thickening of the prosthesis wall cast in that region, and corresponds, for example, to a textured recess 30.

The filler body 210 tailored to the mold cavity 205 may be formed of a ceramic material and is preferably formed by a process of 3-D printing such as that disclosed in applicant's co-pending U.S. patent application, Ser. No. 08/457, 227 filed Jun. 1, 1995and now U.S. Pat. No. 5,687,788, and more generally in U.S. Pat. No. 5,204,055 of Sachs et al.

Figure 4:
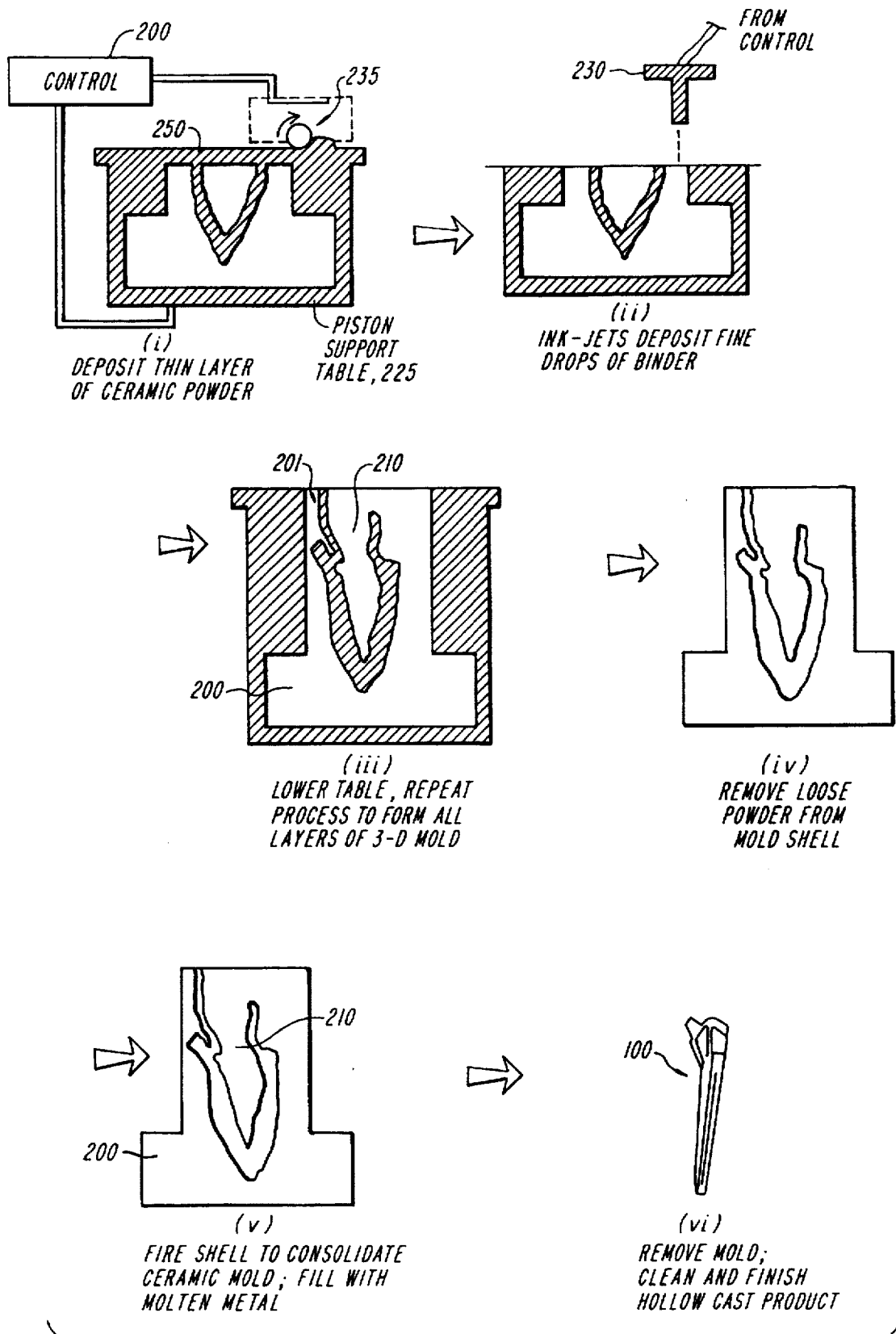
FIG. 4 illustrates a 3-D printing process used for production of a mold for casting the prosthesis.

FIG. 4 illustrates this construction applied, for clarity of illustration, to an entire mold for such a prosthesis. The mold including insert portion 210 is built up layer by layer on a vertically movable table 225 by a process wherein a controller 220 iteratively controls a spreader to deposit a thin layer 250 of ceramic powder and drives a stepper-controlled hardening head 230 in a two dimensional scan across the upper surface over the deposited powder. The head 230 locally hardens part of the thin layer by depositing a liquid but hardenable medium in the thin layer of powder as it moves across the top surface of the plug body 210 under construction and, as illustrated, preferably also over regions radially outward therefrom which are to become the external mold body 200. The hardenable material may be formed by a fine spray of colloidal silica binder ejected from piezo-electrically actuated nozzles in the head 230. In other embodiments, the unconsolidated material may comprise a refractory powder in a curable flowable binder. In the latter case, a laser head may "fix" or harden the binder locally in a pattern by applying heat or light energy thereto. The table 225 is then lowered, and the steps of applying loose powder and selectively applying a curable binder are repeated, and these three steps are repeated sequentially so the plug body 210 is built up layer by layer in successive two dimensional scans across its then current top surface, to form a completed plug insert and mold assembly as shown in FIG. 3 and FIG. 4(iv). It will be understood that the unconsolidated powder is removed and baking or firing are then applied to further bind and stabilize the plug and mold. The body may be consolidated into a solid ceramic by firing at high temperatures. The completed plug body 210 positioned in the center of mold body 200 thus defines a thin shell-like passage between the plug and the mold which is filled with metal in casting the prosthesis of FIG. 2. Following casting, the outer mold block is separated or broken away and the plug body 210 is removed from the cast article, for example, by impact, ultrasonic pulverization, or by some combination of mechanical removal and chemical etching and cleaning techniques. For example, an etch or a differential etch which attacks the material of plug and mold but does not attack the surrounding metal may be used.

Figure 5:
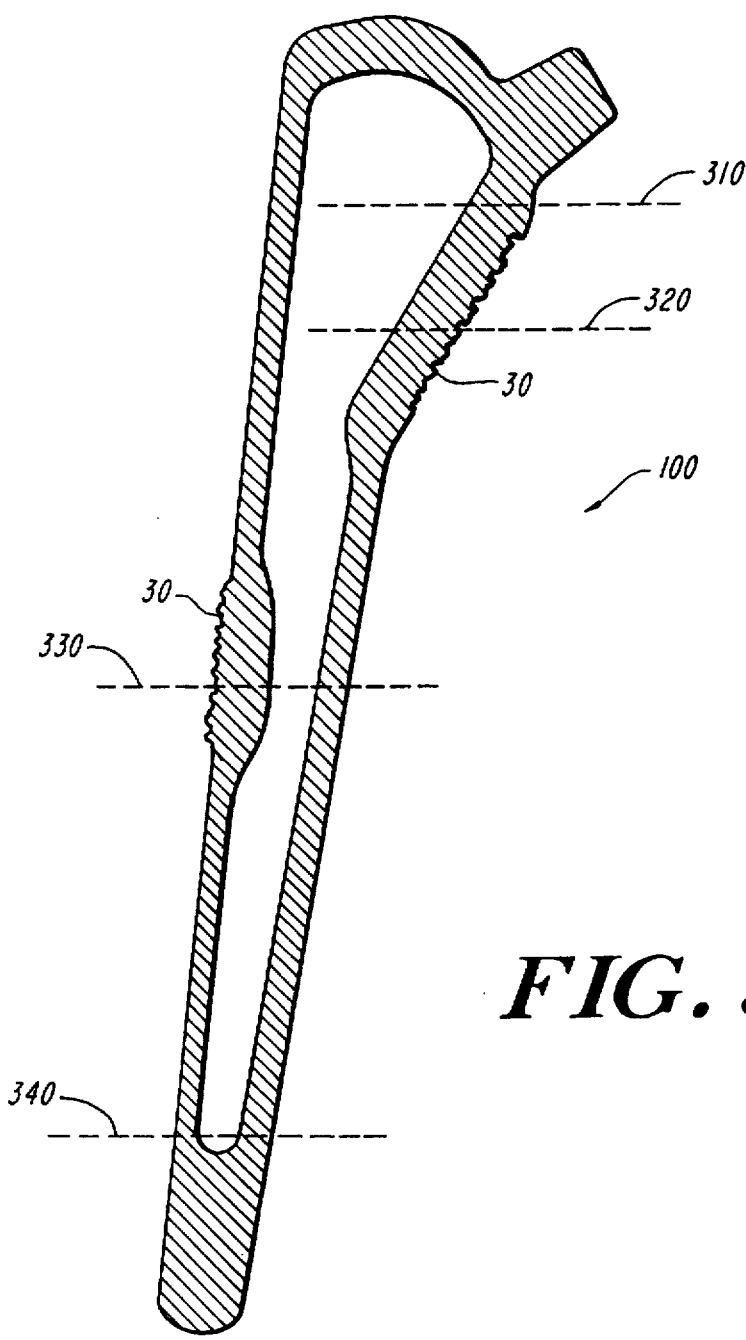
FIG. 5 shows a representative section along the length of the prosthesis.

FIG. 5 is a view similar to FIG. 2 illustrating in greater detail representative wall cross sections of the finished prosthesis. As shown, extending along its length the prosthesis has a number of regions 310, 320, 330, 340 having distinctly different ratios or geometric properties. Thus, in the uppermost region 310 various structural elements such as the post and plug have thick-walled adjacent regions of support, while in the neck 320, the prosthesis has a wide diameter, and a preferentially thickened wall section in the region of the upper texture pocket 30 (FIG. 2). In an intermediate region 330, the body has tapered somewhat but the wall again thickens locally to maintain a suitably high bending stiffness or high wall strength behind another textured region 30. Finally, in the lower region 340, the wall may be of an intermediate thickness or may be entirely solid, distally beyond the end of the hollowing mold plug 210 (FIG. 3). Thus, the wall thickens and thins locally, both along the length of the prosthesis and side-to-side, to simultaneously tailor wall strength and strain transfer to surrounding bone.

The prosthesis in accordance with present invention may largely be constructed by conventional techniques in that the outer body may be formed in the same mold as conventionally used for forming a prosthesis of that size. However, the mold is modified by inclusion of a plug body to displace metal from the central region of the casting. Because this plug body 210 is preferably formed by the process shown in FIG. 4, its dimensions are readily scaled or modified via control 220 so that a similarly shaped but differently dimensioned plug may be built for each size of prosthesis, of a different diameter, such as an eleven millimeter, thirteen millimeter or fifteen millimeter nominal diameter stem. For an item such as a hip prosthesis stem, the "size" may be specified by several parameters, which may correspond, for example, to its taper and nominal diameter. These, as noted above, cover a well-defined range of sizes, for each of which a plug insert is readily constructed to fit within the external contour defined by each mold cavity and yet has a wall thickness calculated to produce effective strain transfer from the prosthesis to surrounding bone. In general, the thickness values are selected to define stiffness parameters approximating those of a natural bone of the size to which the prosthesis is fitted, and these latter stiffness values are readily calculated from the bulk modulus of bone and the bone dimensions. However, a minimal wall thickness (e.g. 2 mm.) is set to assure that at least a minimum threshold of strength will be achieved despite dimensional variations which occur within the range of manufacturing tolerances.

Figure 6:
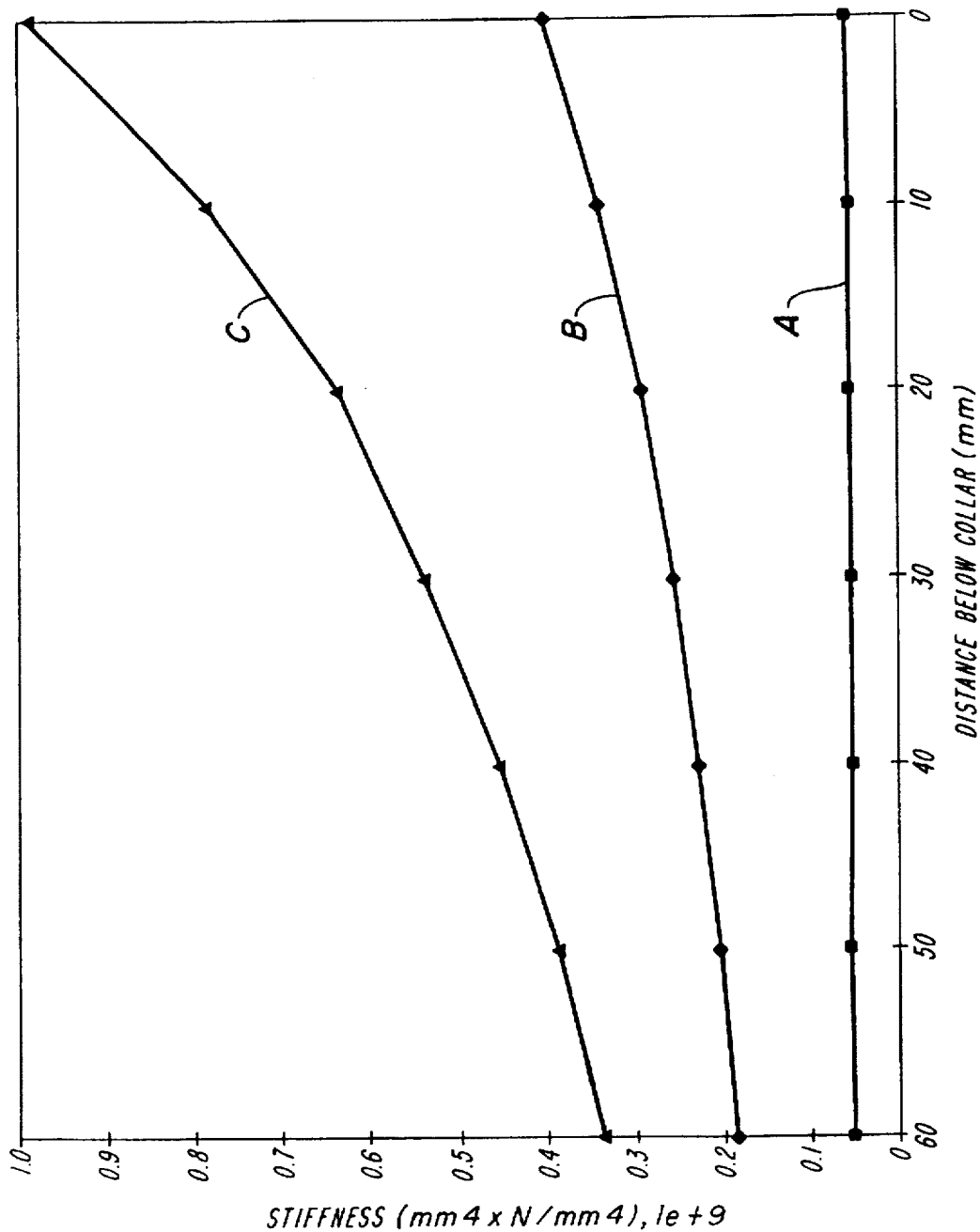
FIG. 6 and 6A plot stiffness of the prosthesis.

FIG. 6 illustrates by way of example in curve A the axial stiffness of a typical bone, about one-half $e^8 mm^4 \times N/mm^4$, and shows a corresponding curve B of stiffness of a prosthesis in accordance with the present invention having a wall thickness on the order of two millimeters and using a titanium alloy. The horizontal axis corresponds to distance below the prosthesis collar. As shown, the wider proximal end has a stiffness above that of bone, but substantially less than ten times as great. In this critical region where stress shielding has conventionally been a problem, the prosthesis may be thinned further or provided with specialized structure such as a ribbed reinforcement of a thin shell to reduce stiffness yet provide adequate local load bearing strength. By way of contrast, the axial stiffness of the solid prosthesis of FIG. 1A is shown in curve C.

Figure 6A:
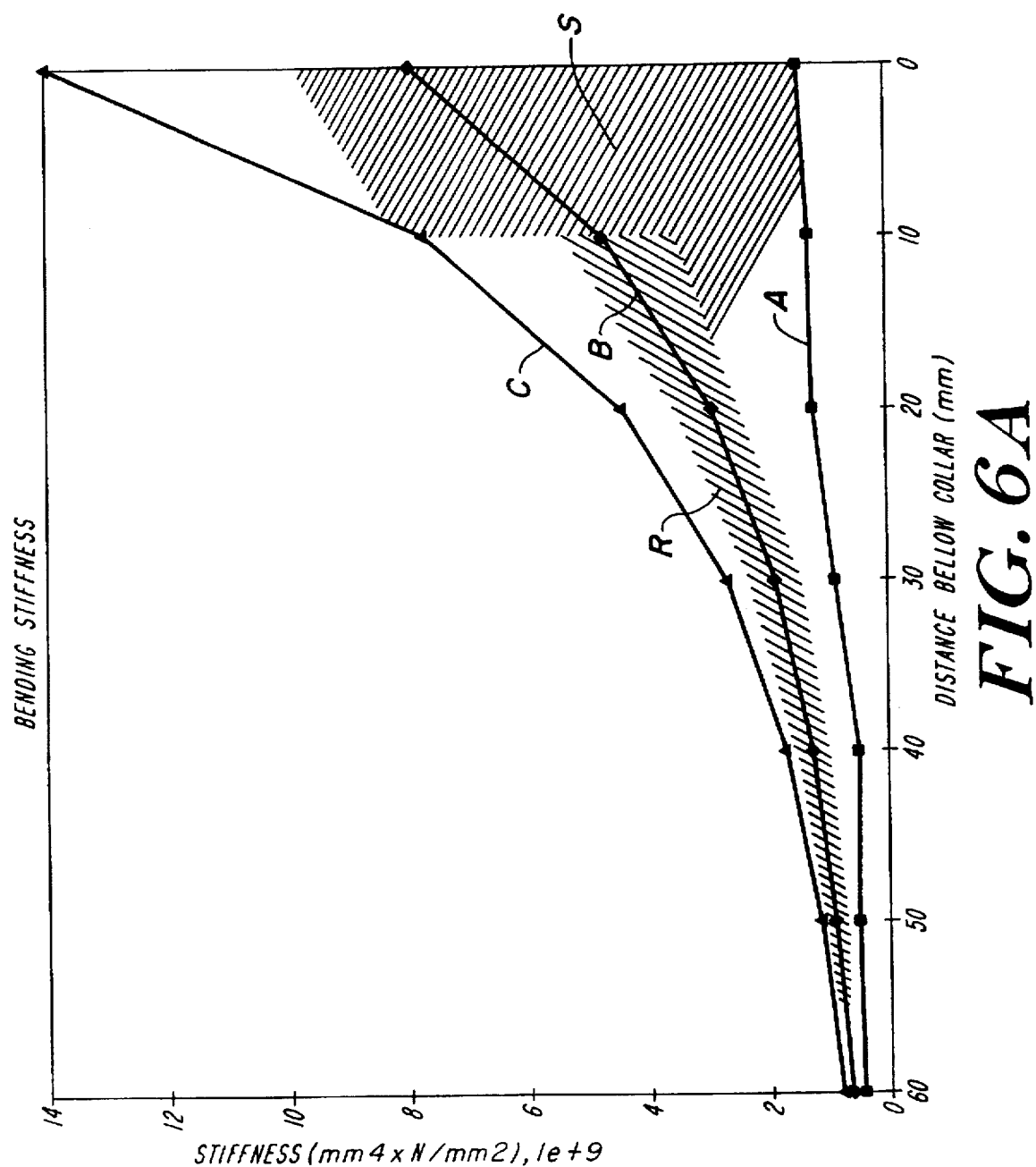

FIG. 6A shows a corresponding graph of bending stiffness modeled for a similarly sized femur (curve B). In each case, the stiffness of a corresponding solid prosthesis is shown (curve C). The prostheses of the present invention generally are characterized by stiffnesses which lie in the region R disposed near curve B, and, at the proximal end, within the region S below curve C. Furthermore the region R generally lies entirely above curve A. However, in a variation of the device, the device may be thinned at one or more intermediate regions to achieve a stiffness of or below that of curve A. This is feasible since the prosthesis need only resist compressive forces during installation, and in a healthy bone the implanted casting will be supported and constrained by surrounding bone so that its mid section need not be full strength. However, a critical concern for such construction will be the maintenance of suitably precise manufacturing tolerances to cast a wall thickness under two millimeters and achieve low stiffness without manufacturing defect.

In general, it is desirable that the axial stiffness, and bending stiffness of the finished prosthesis lie near the curve B shown in FIG. 6, and that the torsional stiffness if applicable to the particular bone under consideration, be similarly matched. In fact, while applicant is not aware of any studies correlating particular (e.g., axial, or torsional) stiffness with bone growth, the process of adjusting structural stiffness by casting a hollow interior in accordance with the present invention is expected to allow one to optimize structural strength while adjusting one stiffness parameter, for example the torsional stiffness, to provide bone stimulation. In practice the characteristics of a finished prosthesis are readily measured, or may be modeled using software such as the program Beam Sections, of Kern International, Inc., Duxbury, Mass., so that the exact contours of the mold plug insert 210 for a given size casting are dependably and readily adjusted to reduce or increase the stiffness at a given point along the prosthesis length to achieve a stiffness of the desired range in the region R.

The invention being thus disclosed in respect of a cast hip stem embodiment, adaptations to other shapes and types of prosthesis will occur to those skilled in the art, as well as variations and modifications for different joints, and different materials and different manufacturing processes. Such adaptations, variations, and modifications are considered to lie within the scope of the invention, as set forth in the claims appended hereto.

What is claimed is:

1. A method of forming a hollow bone prosthesis, such method comprising the steps of:

forming a mold block having a generally tapered cavity corresponding to a desired size of a prosthesis stem, forming a plug body of smaller cross-dimension than said tapered cavity, the plug body having an irregular outer contour, fitting the plug body in the cavity of the mold block, casting metal between the plug body and the mold block to form a metal cast prosthesis, and removing the prosthesis from the mold block and the plug body from the prosthesis to achieve a hollow prosthesis having a stiffness comparable to stiffness of a human bone, wherein the hollow prosthesis has a non-monotomically decreasing interior surface corresponding to the irregular outer contour of the plug body and a wall thickness having at least one region of locally increased thickness.

2. The method of claim 1, further including the step of closing said hollow prosthesis.

3. The method according to claim 1, wherein the prosthesis is a femoral component.

4. The method according to claim 1, wherein the plug body is formed from a refractory material.

5. The method according to claim 1, wherein the plug body is formed using a 3-D printing process.

* * * * *